(12) United States Patent
Skilling

(10) Patent No.: US 6,489,608 B1
(45) Date of Patent: Dec. 3, 2002

(54) METHOD OF DETERMINING PEPTIDE SEQUENCES BY MASS SPECTROMETRY

(75) Inventor: John Skilling, Kenmare (IE)

(73) Assignee: Micromass Limited, Manchester (GB)

( * ) Notice: Subject to any disclaimer, the term of this patent is extended or adjusted under 35 U.S.C. 154(b) by 0 days.

(21) Appl. No.: 09/544,610

(22) Filed: Apr. 6, 2000

(30) Foreign Application Priority Data

Apr. 6, 1999 (GB) ............................................. 9907810
Apr. 16, 1999 (GB) ............................................. 9908684

(51) Int. Cl.$^7$ .......................... B01D 59/44; H01J 49/00
(52) U.S. Cl. ...................................... 250/281; 250/282
(58) Field of Search ................................ 250/281, 282, 250/286, 287, 288

(56) References Cited

U.S. PATENT DOCUMENTS

| | | | |
|---|---|---|---|
| 5,331,158 A | * 7/1994 | Dowell | 250/287 |
| 5,910,655 A | * 6/1999 | Skilling | 250/281 |
| 6,029,114 A | * 2/2000 | Shamovsky et al. | 702/22 |

FOREIGN PATENT DOCUMENTS

| | | |
|---|---|---|
| GB | 2325465 | 11/1998 |
| WO | WO 95/25281 | 9/1995 |

OTHER PUBLICATIONS

Yates III, Journ. of Mass Spectrom., 1998, vol. 33, pp. 1–19.
Papayannopoulos., Mass Spectrom. Rev., 1995, vol. 14, pp. 49–73.
Yates III, McCormack and Eng., Anal. Chem., 1996, vol. 68(17), pp. 534A–540A.
Hunt, Yates III, et al., Proc. Nat. Acad. Sci. USA, 1986, vol. 83, pp. 6233–6237.
Sakurai, Matsuo, Matsuda and Katakuse, Biomed. Mass Spectrom., 1984, vol. 11 (8), pp. 396–399.
Hamm, Wilson and Harvan, CABIOS, 1986, vol. 2(2), pp. 115–118.
Ishikawa and Niwa, Biomed, and Environ. Mass Spectrom., 1986, vol. 13, pp. 373–380.
Taylor and Johnson, Rapid Comm. in Mass Spectrom., 1997, vol. 11, pp. 1067–1075.
Eng et al., J. Am. Soc. Mass Spectrom., 1994, vol. 5, pp. 976–89.
Figeys et al., Rapid Comm. in Mass Spectrom., 1998, vol. 12, pp. 1435–44.
Mortz et al., Proc. Nat. Acad. Sci. USA, 1996, vol. 93, pp. 8264–7.
Shevchenko, Chernushevich et al., Rapid Comm. in Mass Spectrom., 1997, vol. 11, pp. 1015–24.
Yates III, Griffin and Hood, Techniques in Protein Chem. II, 1991, Ch. 46, pp. 477–485.

(List continued on next page.)

*Primary Examiner*—John R. Lee
*Assistant Examiner*—David A. Vanore
(74) *Attorney, Agent, or Firm*—Diederiks & Whitelaw, PLC

(57) ABSTRACT

A method of determining the sequence of amino acids that constitute peptides, polypeptides or proteins by mass spectrometry and especially by tandem mass spectrometry is disclosed without the use of any additional data concerning the nature of the peptide and without any limit to the number of possible sequences considered. The method can be implemented on a personal computer typically used for data acquisition on the tandem mass spectrometer even in the case of peptides comprising 10 or more amino acids. The method does not rely on exhaustive comparison of the spectra predicted from every possible amino acid sequence with any molecular weight constraint, but instead uses mathematical techniques to simulate the effect of such a complete search without actually carrying it out.

36 Claims, 7 Drawing Sheets

OTHER PUBLICATIONS

Sepetov, Issakova et al., Rapid Comm. in Mass Spectrom., 1993, vol. 7, pp. 58–62.

Johnson and Walsh, Protein Science, 1992, vol. 1, pp. 1083–91.

Siegel and Bauman, Biomed. and Environ. Mass Spectrom., 1988, vol. 15, pp. 333–343.

Zidarov, Thibault et al., Biomed. and Environ. Mass Spectrom., 1990, vol. 19, pp. 13–26.

Johnson and Biemann, Biomed. and Environ. Mass Spectrom, 1989, vol. 18, pp. 945–957.

Bartels, Biomed and Environ. Mass Spectrom., 1990, vol. 19, pp. 363–368.

Fernandez–de–Cossio et al., CABIOS, 1995, vol. 11 (4), pp. 427–434.

Hines, Falick et al., J. Am. Soc. Mass Spectrom., 1992, vol. 3, pp. 326–336.

Delgoda and Pulfer, J. Chem. Inf. Computer Sci., 1993, vol. 33, pp. 332–337.

Scarberry, Zhang and Knapp, J. Am. Soc. Mass Spectrom., 1995, vol. 6, pp. 947–961.

Skilling, J. Microscopy, 1998, vol. 190 (1/2), pp. 28–36.

Hastings, Biometrika, 1970, vol. 57, pp. 97–109.

Gelfand and Smith, J. Am. Statis. Assoc., 1990, vol. 85, pp. 398–409.

Smith, Phil. Trans. R. Soc. London A, 1991, vol. 337, pp. 369–386.

Smith and Roberts, J. Royal Statist. Soc. B, 1993, vol. 55 pp. 3–23.

Besag and Green, J. Royal Statist. Soc. B, 1993, vol. 55, pp. 25–37.

Metropolis, Rosenbluth, Rosenbluth, Teller and Teller, J. Chem. Phys., 1953, vol. 21, pp. 1087–1091.

Kirkpatrick, Gelatt and Vecchi, Science, 1983, vol. 220, pp. 671–680.

Aarts and Korst, Simulated Annealing and Boltzmann Machines, Wiley, New York, 1989, pp. 3–114.

Dongre, Eng and Yates III, Trends in Biotechnology, 1997, vol. 15 pp. 418–425.

Yates, Speicher et al., Analytical Biochemistry, 1993, vol. 214, pp. 397–408.

Pappin, Hojrup and Bleasby, Current Biology, 1993, vol. 3(6), pp. 327–332.

Bonner and Shushan, Rapid Comm. in Mass Spectrom., 1995, vol. 9, pp. 1067–1076.

Cossio, Gonzalez and Besada, Biotechnolgia Aplicada, 1995, vol. 12(3), pp. 170–171.

Eng. And Yates, III, Proc. SPIE–int. Soc. Opt. Eng., 1996, vol. 2680, pp. 378–382.

Scoble, Biller and Biemann, Fresenius Z. Anal. Chem., 1987, vol. 327, pp. 239–245.

Yates III, Mao, Griffin and Hood, $39^{th}$ ASMS Conference, 1991, pp. 1233–1234.

Matsuo, Matsuda and Katakuse, Biomed. Mass Spectrom., 1981, vol. 8(4), pp. 137–143.

Matsuo, Sakarai et al., Biomed. Mass Spectrom., 1983, vol. 10(2), pp. 57–61.

Johnson, Ericsson and Walsh, $39^{th}$ ASMS Conference on Mass Spectrom., 1991, pp. 1233–1234.

* cited by examiner

MASS SPECTRUM OF A TRYPTIC DIGEST OF HUMAN TRANSFERRIN PROTEIN

MS/MS SPECTRUM OF m/z 815.4 (+)

MS/MS SPECTRUM OF m/z 815.4 (2+) AFTER MaxEnt 3 PROCESSING

METHOD OF DETERMINING PEPTIDE SEQUENCES BY MASS SPECTROMETRY

BACKGROUND OF THE INVENTION

1. Field of the Invention

A Method of Determining Peptide Sequences by Mass Spectrometry

This invention relates to methods of determining the sequence of amino acids that constitute peptides, polypeptides or proteins by mass spectrometry and especially by tandem mass spectrometry or MS/MS. In particular it relates to methods whereby the sequence can be determined from the mass spectral data alone and which do not require the use of existing libraries of protein sequence information. Methods according to the invention require no information concerning the nature of the peptide other than a library of the amino acid residues that may occur in proteins weighted according to natural abundance.

2. Discussion of the Prior Art

Although several well-established chemical methods for the sequencing of peptides, polypeptides and proteins are known (for example, the Edman degradation), mass spectrometric methods are becoming increasingly important in view of their speed and ease of use. Mass spectrometric methods have been developed to the point at which they are capable of sequencing peptides in a mixture without any prior chemical purification or separation, typically using electrospray ionization and tandem mass spectrometry (MS/MS). For example, see Yates III (J. Mass Spectrom, 1998 vol. 33 pp. 1–19), Papayannopoulos (Mass Spectrom. Rev. 1995, vol. 14 pp. 49–73), and Yates III, McCormack, and Eng (Anal. Chem. 1996 vol. 68 (17) pp. 534A–540A). Thus, in a typical MS/MS sequencing experiment, molecular ions of a particular peptide are selected by the first mass analyzer and fragmented by collisions with neutral gas molecules in a collision cell. The second mass analyzer is then used to record the fragment ion spectrum that generally contains enough information to allow at least a partial, and often the complete, sequence to be determined.

Unfortunately, however, the interpretation of the fragment spectra is not straightforward. Manual interpretation (see, for example, Hunt, Yates III, et al, Proc. Nat. Acad. Sci. USA, 1986, vol. 83 pp 6233–6237 and Papayannopoulos, ibid) requires considerable experience and is time consuming. Consequently, many workers have developed algorithms and computer programs to automate the process, at least in part. The nature of the problem, however, is such that none of those so far developed are able to provide in reasonable time complete sequence information without either requiring some prior knowledge of the chemical structure of the peptide or merely identifying likely candidate sequences in existing protein structure databases. The reason for this will be understood from the following discussion of the nature of the fragment spectra produced.

Typically, the fragment spectrum of a peptide comprises peaks belonging to about half a dozen different ion series each of which correspond to different modes of fragmentation of the peptide parent ion. Each typically (but not invariably) comprises peaks representing the loss of successive amino acid residues from the original peptide ion. Because all but two of the 20 amino acids from which most naturally occurring proteins are comprised have different masses, it is therefore possible to establish the sequence of amino acids from the difference in mass of peaks in any given series which correspond to the successive loss of an amino acid residue from the original peptide. However, difficulties arise in identifying to which series an ion belongs and from a variety of ambiguities that can arrive in assigning the peaks, particularly when certain peaks are either missing or unrecognized. Moreover, other peaks are typically present in a spectrum due to various more complicated fragmentation or rearrangement routes, so that direct assignment of ions is fraught with difficulty. Further, electrospray ionization tends to produce multiply charged ions that appear at correspondingly resealed masses, which further complicates the interpretation of the spectra. Isotopic clusters also lead to proliferation of peaks in the observed spectra. Thus, the direct transformation of a mass spectrum to a sequence is only possible in trivially small peptides.

The reverse route, transforming trial sequences to predicted spectra for comparison with the observed spectrum, should be easier, but has not been fully developed. The number of possible sequences for any peptide ($20^n$, where n is the number of amino acids comprised in the peptide) is very large, so the difficulty of finding the correct sequence for, say, a peptide of a mere 10 amino acids ($20^{10}=10^{13}$ possible sequences) will be appreciated. The number of potential sequences increases very rapidly both with the size of the peptide and with the number (at least 20) of the residues being considered.

Details of the first computer programs for predicting probable amino acid sequences from mass spectral data appeared in 1984 (Sakurai, Matsuo, Matsuda, Katakuse, Biomed. Mass Spectrom, 1984, vol. 11 (8) pp 397–399). This program (PAAS3) searched through all the amino acid sequences whose molecular weights coincided with that of the peptide being examined and identified the most probable sequences with the experimentally observed spectra. Hamm, Wilson and Harvan (CABIOS, 1986 vol. 2 (2) pp 115–118) also developed a similar program.

However, as pointed out by Ishikawa and Niwa (Biomed. and Environ. Mass Spectrom. 1986, vol. 13 pp 373–380), this approach is limited to peptides not exceeding 800 daltons in view of the computer time required to carry out the search. Parekh et al in UK patent application 2,325,465 (published November 1998) have resurrected this idea and give an example of the sequencing of a peptide of 1000 daltons which required $2\times10^6$ possible sequences to be searched, but do not specify the computer time required. Nevertheless, despite the increase in the processing speed of computers between 1984 and 1999, a simple search of all possible sequences for a peptide of molecular weights greater than 1200 daltons is still impractical in a reasonable time using the personal computer typically supplied for data processing with most commercial mass spectrometers.

This problem has long been recognized and many attempts have been made to render the problem more tractable. For example, the MS/MS spectrum may be correlated with amino acid sequences derived from a protein database rather than every possible sequence. Such methods are taught in PCT patent application 95/25281, by Taylor and Johnson (Rapid Commun. in Mass Spectrom. 1997 vol. 11 pp 1067–1075, by Eng. McCormack, Yates in J. Am. Mass Spectrom. 1994 vol. 5 pp 976–989, by Figeys, Lock et al. (Rapid Commun. in Mass Spectrom. 1998 vol. 12 pp 1435–1444), and by Mortz, O'Connor et al (Proc. Nat. Acid Sci. USA 1996 vol. 93 pp 8264–8267). Alternatively, MS/MS experiments can be carried out on both the original peptide and a derivative of it, and the results from both experiments combined to establish at least a partial sequence without reference to a database. (See, for example, the isotopic labeling method taught by Shevchenko, Chernushevich et al in Rapid Commun. in Mass Spectrom, 1997 vol. 11 pp 1015–24, or the esterification method taught by Yates III, Griffin and Hood in Techniques in Protein Chem. II, ch 46 (1991) pp 477–485), and the $H_2/D_2$ exchange method taught by Septov, Issakova et al in Rapid Commun. in Mass Spectrom. 1993 vol. 7 pp 58–62. Johnson and Walsh (Protein Science, 1992 vol. 1 pp 1083–1091) teach a similar method, combining Edman degradation data and MS/MS data.

Of the prior programs which attempt to predict sequence information using only MS/MS data and without reference to existing databases, a variety of methods have been suggested to facilitate the prediction of sequence information. Siegel and Bauman (Biomed. Environ. Mass Spectrom. 1998 vol. 15 pp 333–343) describe an algorithm which builds up the sequence information stepwise from the mass difference between neighbouring ions in ion series recognized in the spectrum, but good results were obtained only with peptides of a few amino acids. Zidarov, Thibault et al. (Biomed. and Environ. Mass Spectrom, 1990 vol. 19 pp 13–26) proposed an algorithm which first attempted to derive the amino acid composition of the peptide from molecular weight and isotopic ratio data, and subsequently to sequence the peptide using a stepwise approach considering all possible sequences for the amino acids so identified. The program SEQPEP (Johnson and Biemann, Biomed and Environ. Mass Spectros. 1989 vol. 18 pp 945–957) identified short sub-sequences of amino acids in a peptide and then extended the sequence outwards from the ends of the sequence, attempting to correlate other peaks in the spectra with more amino acid residues, until the molecular weight of the peptide was reached. Bartels (Biomed. and Environ. Mass Spectrom, 1990 vol. 19 pp 363–368) recognized this search strategy as a problem in graph theory, and the method was further developed by Fernandez-de-Cossio et al (CABIOS, 1995 vol. 11 (4) pp 427–434). These methods calculated a score for trial sequences based on the number of peaks in the experimental spectrum that they fit. Unfortunately, peptides fragment in idiosyncratic fashion, and global scores such as theirs do not perform well. Hines, Falik, et al (J. Am. Soc. Mass Spectrom 1992 vol. 3 pp 326–336) have described a sequencing program which uses pattern recognition techniques to identify groups of peaks in an observed spectrum and subsequently to predict the amino acid sequence. Delgada and Pulfer (J. Chem. Inf. Computer Sci. 1993 vol. 33 pp 332–337) describe a similar pattern recognition algorithm which uses learning machine techniques, also applied to observed spectra. Scarberry, Zhang and Knapp (J. Am. Soc. Mass Spectrom, 1995 vol. 6 pp 936–946) report the application of artificial neural networks to classify the peaks in observed peptide MS/MS spectra followed by sequence determination of the series of peaks so identified.

The following difficulties are inherent in these prior sequencing algorithms. Those that are limited to searching existing databases to identify a peptide or protein will clearly fail if the sequence is in fact unknown at the time. Those that attempt to sequence in a stepwise manner will fail if the spectrum does not contain a significant peak at a mass corresponding to a particular amino acid loss, and the likelihood of this increases rapidly as the number of amino acids comprised in the peptide increases. Those that require the analysis of derivatives of the peptides to resolve ambiguities are clearly less desirable than those which purport to provide the sequence without such derivatives. Those that eliminate groups of possible sequences early on in the sequencing process on the basis of a single test in order to rapidly reduce the number of possibilities to a more manageable level frequently fail to suggest even a low probability for the correct sequence because it has been incorrectly eliminated due to failure of that test. This may arise due to an incorrect assignment of a peak to a series, a smaller than expected peak intensity, or slightly inaccurate mass measurement. Those that require additional information, such as a partial sequence, will fail if that information is in fact incorrect or unavailable. Those that attempt to recognize patterns in the observed data are heavily dependent on a precise understanding of the fragmentation mechanisms which determine the nature of the spectrum, and the complexity of the processes involved is such that universally applicable rules cannot at present be formulated. Thus, the resurrection in GB 2,325,465 of the "de-novo" approach of Sakurai et al, Ishikawa, et al and Hamm et al (ibid.) whereby all possible sequences are compared with the observed data without eliminating any possibilities nor relying on a machine interpretation of chemical rules is clearly desirable. However, GB 2,325,465 does not advance the art in practice and merely restates the earlier techniques.

Thus, there is no prior teaching of a "de-novo" peptide sequencing method for MS/MS spectra which is capable of handling the data from peptides of more than about ten amino acids. Full searches take too long on the computer typically used to process data generated by the mass spectrometer used to obtain the MS/MS data.

SUMMARY OF THE INVENTION

It is an object of the present invention to provide a method of sequencing a peptide either individually or comprised in a mixture of peptides, by tandem mass spectrometry without the use of any additional data concerning the nature of the peptide and without any limit to the number of possible sequences considered. It is a further object to provide such a method which can be implemented on a personal computer typically used for data acquisition on the tandem mass spectrometer, even in the case of peptides comprising 10 or more amino acids. It is another object to provide such a method which does not rely on exhaustive comparison of the spectra predicted from every possible amino acid sequence consistent with any molecular weight constraint, but instead uses mathematical techniques to simulate the effect of such a complete search without actually carrying it out.

In accordance with these objectives the invention provides a method of identifying the most likely amino acid sequences which would account for a mass spectrum obtained from a peptide of unknown sequence, said method comprising the steps of:

a) Producing a processable mass spectrum from said peptide;

b) Choosing a limited number of trial amino-acid sequences which are consistent with a prior probability distribution;

c) Iteratively modifying said trial sequences through a terminated Markov Chain Monte Carlo (MCMC) algorithm to generate new trial sequences, using at each stage modifications which lie within said prior probability distribution, calculating the probability of each of said trial sequences accounting for said processable mass spectrum, and accepting or rejecting each of said trial sequences according to said probability and the mathematical principle of detailed balance.

In preferred methods, the probability of a particular trial sequence accounting for the processable mass spectrum is estimated using Bayes' theorem. A prior probability is assigned to the sequence and is multiplied by a likelihood factor that reflects the degree of agreement between a spectrum predicted for that sequence and the processable mass spectrum. This process is represented by the equation Probability (trial sequence AND processable spectrum)=Prior (trial sequence)×Probability (processable spectrum GIVEN trial sequence)

Conveniently, the term

Prior (trial sequence)

may be determined from the natural (or other) abundance of each of the amino acid residues comprised in the trial sequence. The term Probability (processable spectrum GIVEN trial sequence)

is the likelihood factor and may be determined using a fragmentation model that sums probabilistically over all the ways in which a trial sequence might fragment and give rise to peaks in the processable mass spectrum.

In one preferred embodiment, the limited number of trial amino-acid sequences chosen in step b) may comprise about 100 members chosen pseudo-randomly from the prior probability distribution. This distribution may comprise sequences based on a library of the 20 most common amino acid residues, but it is within the scope of the invention to include less common or presently unknown residues. The distribution embodies rough preliminary information about the nature of the unknown peptide sample, but its determination may require only minimal information about the sample. For example, it may be sufficient that trial sequences chosen from it are chemically plausible and not of such length that they obviously could not represent the sample. The amino acid composition of the sample, if known, may also suffice. In preferred methods, however, the distribution may be constrained by the approximate molecular weight of the sample, for example within ±5 daltons, or most preferably within ±0.5 daltons if it is known sufficiently accurately. In general, the more constraints that can be placed on the prior probability distribution, the faster will be the computation and the more tightly constrained will be the most probable sequences for the unknown peptide.

It will be understood that in the initial stages of the process the trial sequences may bear little resemblance to the actual sequence of the unknown peptide. In order to ensure a gentle convergence to the most probable sequences, in further preferred methods the contribution of the likelihood factor to the probability score may be controlled by simulated annealing. Typically, the likelihood factor may be raised to a fractional power which is initially zero and is gradually increased as the algorithm progresses so that the experimental data is given gradually increasing significance.

A further advantage in the use of simulated annealing is that the algorithm employed can indicate when a sufficient number of trial sequences have been tested, so that the generation of trial sequences may be terminated automatically. The simulated annealing algorithm may itself, on the basis of the probabilities assigned to previously tested sequences, determine the fractional power to be currently applied to the likelihood factors of the current trial sequences. Thus in further preferred embodiments of the invention the generation and testing of new trial sequences is continued until the simulated annealing algorithm sets to the correct value (unity) the power to which the likelihood factors are raised.

According to the invention, a Markov Chain Monte Carlo algorithm generates new trial amino-acid sequences. Use of such an algorithm allows the most probable sequences to be identified without the need to test every possible sequence of amino acids that might, for example, account for the observed molecular weight range of the unknown peptide. In order to achieve maximum efficiency, the changes made to the trial sequences should preferably be made in a chemically meaningful manner, rather than purely randomly. Thus, in further preferred embodiments of invention, the Markov Chain Monte Carlo algorithm may modify a trial sequence in at least some, and preferably all, of the following ways:

a) Reversing a contiguous sub-sequence with randomly chosen end points, for example a sequence . . . ARQEIK . . . may be changed to . . . KIEQRA . . .

b) Cycling a contiguous sub-sequence with randomly chosen end points, for example . . . ARQEIK . . . may be changed to . . . QEIKAR . . .

c) Permuting a contiguous sub-sequence with randomly chosen end points, for example a sequence . . . ARQEIK . . . may be changed to . . . IQRKAE . . .

d) Replacing a contiguous sub-sequence with randomly chosen end points with another sub-sequence of approximately the same nominal mass, for example . . . NEQ . . . may be replaced by . . . EKGG . . .

e) Exchanging the C-terminus and N-terminus ends of two sequences to preserve nominal mass, for example the sequences EKGG-DQCYKR and NEH-YKDQCR may be changed to NEH-DQCYKR and EKGG-YKDQCR.

It will be appreciated that this list of possible mutations is not exclusive and many others may be included in the Markov Chain Monte Carlo algorithm. However, to minimize the danger of the algorithm failing to explore all the regions of high probability of the trial sequences accounting for the processable mass spectrum, it is desirable that at least one "genetic algorithm", as exemplified by the mutation e) above, is included. In accordance with the Markov Chain Monte Carlo method, the choice of which mutations to make to a particular sequence may be determined by a pseudo-random number generator.

In still further preferred methods, a novel fragmentation model, which sums probabilistically over all the ways in which a trial sequence might fragment to give rise to peaks in the processable mass spectrum, is employed. Such a model may be based on the production of at least two series of ions, the b series (which comprises ions representing the N-terminal residue of the trial sequence and the loss of C-terminal amino acid residues), and the y" series (which comprises ions representing the C-terminal residue and the loss of N-terminal amino acid residues). Each family of ions behaves as a coherent series, with neighbouring ions likely to be either both present or both absent. This behaviour may be described by a Markov chain, in which the probability of an ion being observed is influenced by whether or not its predecessor was observed. The parameters of the chain may be adjusted to take account of the proton affinities of the residues and their physical bond strengths. The fragmentation model may be refined by including other ion series, particularly the a series (b ions which have lost CO), the z" series (y" ions which have lost $NH_3$), and the more general loss of $NH_3$ or $H_2O$, again taking account of the probability of the chemical processes involved. Immonium ions equivalent to the loss of CO and H from the various amino acid residues may also be included. Further, the fragmentation model may comprise the generation of sub-sequences of amino acids, that is, sequences that begin and end at amino acid residues internal to the unknown peptide. It will be appreciated that the more realistic is the fragmentation model, the better will be the accuracy and speed of the computation of the most probable sequences. It is theirfore envisaged that different fragmentation models may be employed if advances are made in understanding the chemical mechanism by which the mass spectrum of the petide is produced.

Using Marov chains to model the fragmentation process allows the sum over all the possible fragmention patterns to be calculated in liner time (ie, in a time proportional to the number of animo acid residues in the peptide) rather than in a time proportional to the exponentially large number of fragmentation patterns themselves. This allows the time taken for the prediction of the most probable sequences to be reduced to a practical value (that is, a minute or so), even for peptides of 10 or more amino acids, using a typical personal computer. However, it will be appreciated that the invention is not limited to the particular fragmentation model described above, but includes any probabilistic fragmentation model that can be integrated computationally in polynomial time. The result of applying such a model is a probabilistic likelihood factor Probability(processable spectrum GIVEN trial sequence) that can be used in the Markov Chain Monte Carlo algorithm.

Although in certain simple cases the processable mass spectrum may simply be the observed mass spectrum, it is generally preferable to convert the observed spectrum into a more suitable form before attempting to sequence the peptide. Preferably, the processable spectrum is obtained by converting multiply-charged ions and isotopic clusters of ions to a single intensity value at the mass-to-charge ratio corresponding to a singly-charged ion of the lowest mass isotope, and calculating an uncertainty value for the actual mass and the probability that a peak at that mass-to-charge ratio has actually been observed. Conveniently, the uncertainty value of a peak may be based on the standard deviation of a Gaussian peak representing the processed peak and the probability that a peak is actually observed may be related to the signal-to-noise ratio of the peak in the observed spectrum. The program "MaxEnt3™" available from Micromass UK Ltd. may be used to produce the processable spectrum from an observed spectrum.

It will be appreciated that a fragmentation model as described may be used to calculate the probability of any trial sequence of amino acids accounting for a given mass spectrum, irrespective of how that trial sequence has been derived. Viewed from another aspect, therefore, the invention comprises a method of calculating the probability that an experimentally determined mass spectrum of a peptide or a similar molecule may be accounted for by a given sequence of amino acids by the use of a fragmentation model which sums probabilistically over all the ways that said given sequence might fragment. Preferably, the fragmentation model may model the fragmentation of the sequence by means of Markov chains in the manner described above. Also preferably, the experimentally determined mass spectrum is a processable spectrum, obtained in the manner described above. For example, a fragmentation model according to the invention may be used to calculate the probability of amino acid sequences comprised in an existing protein or peptide database accounting for an experimentally observed mass spectrum of a peptide. In this way the peptide, and/or the protein from which it is derived, may be identified. Conveniently, in such a method, only sequences or partial sequences having a molecular weight in a given range are selected from the database for input to the fragmentation model.

In order to carry out the methods of the invention a sample comprising one or more unknown peptides may be introduced into a tandem mass spectrometer and ionized using electrospray ionization. The molecular weights of the unknown peptides may typically be determined by observing the molecular ion groups of peaks in a mass spectrum of the sample. The first analyzer of the tandem mass spectrometer may then be set to transmit the molecular ion group of peaks corresponding to one of the unknown peptides to a collision cell, in which the molecular ions are fragmented by collision with neutral gas molecules. The second mass analyzer of the tandem mass spectrometer may then be used to record an observed fragmentation mass spectrum of the peptide. A processable mass spectrum may then be derived from the observed spectrum using suitable computer software, as explained. If the sample comprises a mixture of peptides, for example as might be produced by a tryptic digest of a protein, further peptides may be analyzed by selecting the appropriate molecular ion group using the first mass analyzer.

Viewed from another aspect the invention provides apparatus for identifying the most likely sequences of amino acids in an unknown peptide, said apparatus comprising a mass spectrometer for generating a mass spectrum of a said unknown peptide and data processing means programmed to:

a) Process data generated by said mass spectrometer to produce a processable mass spectrum;

b) Choose a limited number of trial amino acid sequences that are consistent with a prior probability distribution;

c) Iteratively modify said trial sequences through a terminated Markov Chain Monte Carlo algorithm to generate further trial sequences which are consistent with said prior probability distribution, to calculate the probability of each of said trial sequences accounting for said processable mass spectrum and to accept or reject each of said trial sequences according to said probability and the mathematical principle of detailed balance.

In preferred embodiments, apparatus according to the invention comprises a tandem mass spectrometer, and most preferably a tandem mass spectrometer that comprises a Time-of-Flight mass analyzer at least as its final stage. A Time-of-Flight mass analyzer is preferred because it is generally capable of greater mass measurement accuracy than a quadrupole analyzer. Preferably also the mass spectrometer comprises an electrospray ionization source into which an unknown peptide sample may be introduced.

BRIEF DESCRIPTION OF THE DRAWINGS

A preferred method of the invention will now be described in greater detail by reference to the figures, wherein.

DETAILED DESCRIPTION OF THE PREFERRED EMBODIMENT

Figure 1:
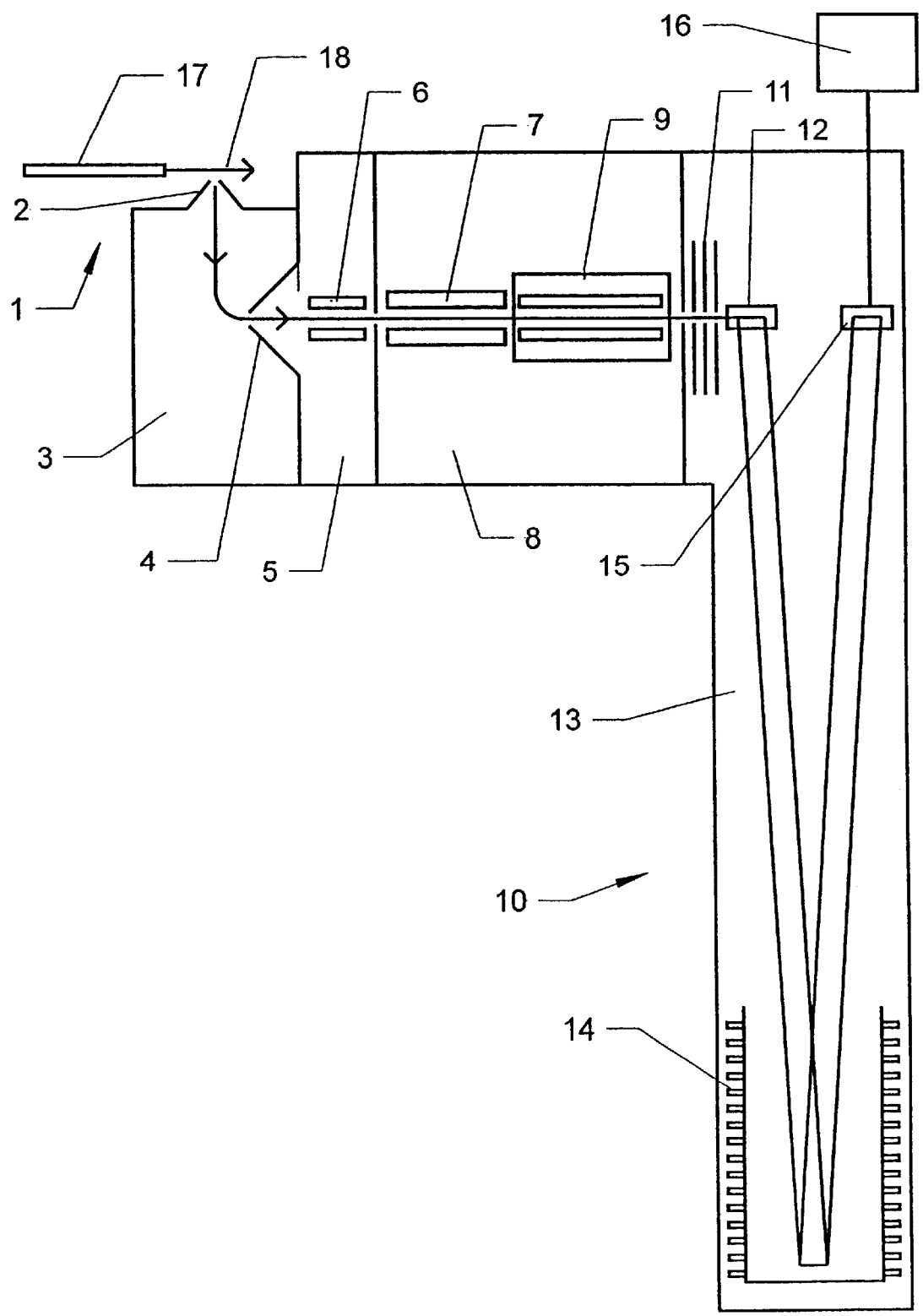
FIG. 1 is a schematic drawing of a tandem TOF mass spectrometer suitable for generating a mass spectrum from an unknown peptide sample.

Referring first to FIG. 1, the principal components of a tandem time-of-flight mass spectrometer suitable for carrying out methods according to the invention are shown in chematic form. An unknown peptide sample, or a mixture of such samples, is introduced into a capillary 17 comprised in an electrospray ion source generally indicated by 1. A jet 18 comprising ions characteristic of said peptide is generated in the source 1, and at least some of these ions pass through an aperture in a sampling cone 2 into a first evacuated chamber 3. From the chamber 3 the ions pass through an aperture in a skimmer cone 4 into a second evacuated chamber 5, and are then transported by means of a hexapole ion guide 6 into a quadrupole mass analyzer 7 disposed in a third evacuated chamber 8.

In a spectrometer of the kind illustrated in FIG. 1, the molecular weight of the peptide may be determined by using the mass analyzer 7 in a non mass-selective mode while a mass spectrum of the sample is acquired. Preferably, the molecular weight is determined to within ±0.5 daltons.

In order to record a fragmentation spectrum of an unknown peptide, the mass analyzer 7 may be set to transmit only the molecular ions of the unknown peptide (or a selected one of several peptides, if more than one is present in the sample). Molecular ions of the unknown peptide then pass from the mass analyzer 7 into a hexapole collision cell 9 which contains a collision gas (typically helium or argon) at a pressure between $10^{-3}$ and $10^{-2}$ torr and are fragmented to produce fragment ions which are indicative of the sequence of the unknown peptide. Typically, these fragment ions include ions formed by various losses of the amino acid residues from both the C and N termini of the peptide molecule, as discussed in more detail below.

The fragment ions formed in the collision cell 9 pass into a time-of-flight mass analyzer generally indicated by 10 via an electrostatic lens 11. In the time-of-flight analyzer 10, the ions are received by an ion-pusher 12 which causes bunches of ions to travel through a drift region 13 from the pusher to an ion-reflector 14, then back to an ion detector 15, as shown in FIG. 1. The mass of the ions is then determined by measuring the time taken for them to reach the detector 15 relative to the time they were ejected from the ion-pusher 12. A data acquisition system 16 controls this process and is programmed to carry out a method of the invention as discussed below. The mass range of the entire spectrometer should be at least 2500 daltons and it should preferably be capable of determining the masses of the fragment ions to at least ±0.5, and preferably ±0.05 daltons. A suitable mass spectrometer is obtainable from Micromass UK Ltd as the "Q-T of".

Figure 2:
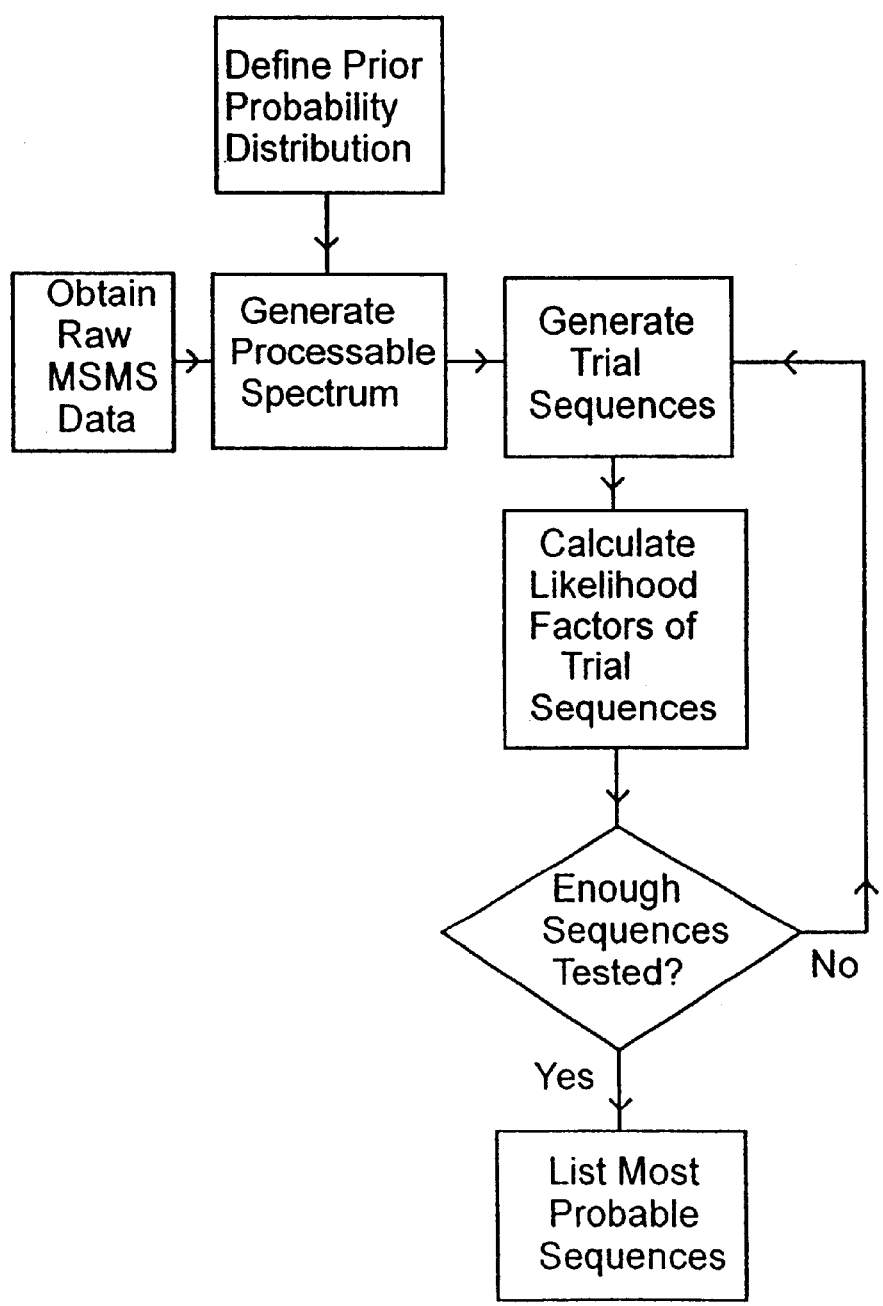
FIG. 2 is a flow chart representing the operation of a method according to the invention.

Referring next to FIG. 2, a preferred method according to the invention begins by acquiring fragmentation mass spectrum of the unknown, peptide using the tandem mass spectrometer of FIG. 1.

The fragmentation spectrum is in practice complicated by the occurrence of multiply-charged ions and isotopic clusters (that is, several peaks associated with a single ion of a particular nominal mass consequent upon the natural abundance of different carbon, hydrogen, oxygen, nitrogen, and sulphur isotopes comprised in the ion). The method is therefore facilitated by conversion of the raw fragmentation spectrum to a "processable" spectrum. In such a spectrum, the multiply-charged ions may be converted to a corresponding singly charged ion at the appropriate nominal mass and the minor peaks comprised in each isotopic cluster are subsumed into the main peak representing the parent isotopic variant (i.e. that comprising $^{12}C$, $^{16}O$, $^{15}N$, $^{1}H$, $^{32}S$). The program "MaxEnt3™" available from Micromass UK Ltd. may be used for this purpose, but other software capable of these operations may be employed.

It is also preferable to represent each peak in the processable mass spectrum as a single nominal mass value together with an uncertainty value, for example 512.30±0.05 daltons, rather than as a series of real data points forming an approximately Gaussian peak as it would appear in the raw spectrum. The program "MaxEnt3™" also carries out this conversion, but any suitable peak recognition software could be employed. However, it has been found that the fidelity of the final most probable sequences predicted by methods according to the invention in strongly dependent on the range of the masses assigned to the constituent peaks in the processable mass spectrum. Consequently, both the calibration of the mass scale of the tandem mass spectrometer and the conversion of the raw peaks to their normal masses and their uncertainties must be carried out carefully and rigorously. It has been found that the intensities of the peaks in the fragmentation spectrum have little value in predicting the sequence of an unknown peptide. Instead of intensities, therefore, the peak recognition software should calculate a probability that each peak actually has been detected in the fragmentation spectrum, rather than being due to noise or an interfering background. The program "MaxEnt3™" is also capable of this operation.

In order to predict the sequence of the unknown peptide, an initial set of approximately 100 trial sequences is first generated by building them pseudo-randomly according to the constraints imposed by the prior probability distribution. The sequences comprised in this initial set are based on pseudo-random combinations of the amino acid residues comprised in a library and may be assigned probabilities that reflect the natural abundance of the amino acids concerned. The library typically comprises the 20 most common amino acids or chemical modifications to the most common acids if desired. Table 1 lists those amino acids along with their molecular weights.

TABLE 1

20 most commonly occurring amino acid residues

| Symbol | Name | Molecular formula | Monoisotopic mass | Natural Abundance (%) |
|---|---|---|---|---|
| A | Alanine | $C_3H_5NO$ | 71.037 | 7.58 |
| R | Arginine | $C_6H_{12}N_4O$ | 156.101 | 5.16 |
| N | Asparagine | $C_4H_6N_2O_2$ | 114.043 | 4.45 |
| D | Aspartic Acid | $C_4H_5NO_3$ | 115.027 | 5.28 |
| C | Cysteine | $C_3H_5NOS$ | 103.009 | 1.66 |
| Q | Glutamine | $C_5H_8N_2O_2$ | 128.059 | 3.97 |
| E | Glutamic Acid | $C_5H_7NO_3$ | 129.043 | 6.37 |
| G | Glycine | $C_2H_3NO$ | 57.021 | 6.84 |
| H | Histidine | $C_6H_7N_3O$ | 137.059 | 2.25 |
| I | Isoleucine | $C_6H_{11}NO$ | 113.084 | 5.81 |
| L | Leucine | $C_6H_{11}NO$ | 113.084 | 9.42 |
| K | Lysine | $C_6H_{12}N_2O$ | 128.095 | 5.95 |
| M | Methionine | $C_5H_9NOS$ | 131.040 | 2.37 |
| F | Phenylalanine | $C_9H_9NO$ | 147.068 | 4.09 |
| P | Proline | $C_5H_7NO$ | 97.053 | 4.90 |
| S | Serine | $C_3H_5NO_2$ | 87.032 | 7.12 |
| T | Threonine | $C_4H_7NO_2$ | 101.048 | 5.67 |
| W | Tryptophan | $C_{11}H_{10}N_2O$ | 186.079 | 1.23 |

TABLE 1-continued 20 most commonly occurring amino acid residues

| Symbol | Name | Molecular formula | Monoisotopic mass | Natural Abundance (%) |
|---|---|---|---|---|
| Y | Tyrosine | $C_9H_9NO_2$ | 163.063 | 3.18 |
| V | Valine | $C_5H_9NO$ | 99.068 | 6.58 |

The prior probability that is assigned to each trial sequence is calculated by multiplying the probabilities (which must always lie in the range $0 \leq p \leq 1$) of each of the amino acids in the sequences, for example, the sequence ETDDCQ would be assigned a prior probability of $$0.0637 \times 0.0567 \times 0.0528 \times 0.0528 \times 0.166 \times 0.0397 = 6.63 \times 10^{-9}$$

on the basis of the natural abundance shown in table 1.

The initial set of the trial sequences is additionally constrained by the molecular weight of the peptide that is known from the mass spectrum produced by the first mass analyzer (FIG. 1). In order to limit the trial sequences to a given molecular weight window (typically ±0.5 daltons), a sub-library of pre-computed partial sequences having different molecular weights <700 daltons is first prepared and indexed according to the molecular weight. Trial sequences are then randomly built up residue by residue until the sum of the molecular weights differs by less then 700 daltons from molecular weight of the unknown peptide. The trial sequence is then completed by one of the pre-computed sequences whose molecular weight is approximately equal to the difference between the partially completed sequence and that of the peptide. As a further refinement, the entire trial sequence may then be pseudo-randomly permuted in order to minimize bias against a heavy residue such as tryptophan at the end of the sequence.

The next stage of the method is to compare each of the trial sequences with the processable spectrum and calculate a probability that each sequence accounts for the spectrum using Bayes' theorem. As explained, this is done by multiplying the prior probability as calculated above by a likelihood factor which reflects the actual degree of agreement between a spectrum predicted from the trial sequence and the processable spectrum, that is:

Probability (trial sequence, processable spectrum)=Prior (trial sequence)×Probability (processable spectrum GIVEN trial sequence)

The latter term is the likelihood factor. Estimation of likelihood factors is discussed in detail below. New trial sequences are then generated using a Markov Chain Monte Carlo (MCMC) algorithm and the probability of these sequences is calculated as described.

The application of MCMC algorithms to experimental scientific data is reviewed by Skilling in J. Microscopy 1998 vol. 190 (½) pp 28–36. In the present invention, use of such an algorithm simulates the exploration of huge numbers of possible sequences by taking the trial sequences and altering them in a pseudo-random manner to generate new trial sequences. Each of the new sequences so generated must of course fall within the constraints imposed by the prior probability distribution discussed previously, particularly as regards molecular weight. A new sequence is accepted if the probability of a match between a spectrum predicted from it is thereby increased, or possibly accepted if it is decreased, in accordance with the mathematical principle of detailed balance which is inherent in all suitable algorithms. Trial sequences with the lowest probabilities progressively disappear from the computations so that as the algorithm progresses the probability of particular sequences appearing in the computation evolves to mirror the probability assigned to them by the Bayesian approach outlined above. The most probable sequences predicted at any stage while the algorithm is running can be determined by causing the computer running the algorithm to output a list of the sequences presently undergoing changes at that time.

The most probable sequences thus identified will eventually correspond to the most probable sequences for the unknown peptide based on its tandem mass spectrum, and the algorithm may then be terminated. A more precise way of terminating the MCMC algorithm is discussed below.

Put another way, as it progresses the algorithm learns to avoid domains of potential sequences which have low probabilities and comes to diffuse amongst a relatively few plausible sequences which have high probabilities. MCMC algorithms achieve this without specifically testing all possible sequences because changes which lead in the direction of new sequences with lower probabilities are eventually rejected before extensive modifications to those lower probability sequences (which would result in sequences of even lower probability) are made. In the present preferred method, Markov Chains are started from each of the initial set of 100 trial sequences and the total number of sequences available for alteration is maintained around the 100 figure, rejecting the lowest probability sequences so generated and concentrating on those of the highest probability. As the algorithm progresses, therefore, it tends to lose all memory of the initial set of sequences.

The mathematical details of suitable MCMC algorithms have been given by Hastings, in Biometrika 1970 vol. 57 pp 97–109, Gelfand and Smith in J. Am. Statis. Assoc. 1990 vol. 85 pp 398–409, Smith in Philos. Trans. R. Soc. London A, 1991 vol. 337 pp 369–386, Smith and Roberts in J. Royal Statis. Soc. B, 1993 vol. 55 pp 3–23, and Besag and Green in J. Royal. Statis. Soc. B 1993 vol. 55 pp 25–37.

In particular, MCMC algorithms incorporating a Metropolis algorithm (Metropolis, Rosenbluth, Rosenbluth, Teller and Teller, J. Chem. Phys., 1953, vol. 21 pp 1087–1091) has been found most suitable for use in methods according to the present invention.

It is very important for efficient exploration of plausible sequences that the changes made by the MCMC algorithm are appropriate. Meaningful ways in which a sequence can be modified have been discussed above. Incorporating these mutations in the MCMC algorithm has been found to give accurate sequence predictions in most of the cases tested with less than 5 minutes computation time, but it is within the scope of the invention to incorporate other chemically plausible mutations either to replace some of the proposed mutations or in addition to them.

In the preferred method, simulated annealing (see, for example, Kirkpatrick, Gelaft, Vecchi, Science, 1983, vol. 220, pp 671–680 and Aarts, Kost in Simulated Annealing and Boltzmann Machines, Wiley, New York, 1989) is used to ensure that the MCMC algorithm converges properly to the most probable sequences. As explained, in calculating the probability of a trial sequence the likelihood factor is raised to a power which is initially set to zero and gradually increased to unity as the MCMC algorithm progresses, thereby gradually increasing the importance of the experimental data from no significance to maximum significance. The schedule for increasing the fractional power $\lambda$ is as follows. Given a current set of N trial sequences with likelihood values $L_1, \ldots, L_N$, a central likelihood value $L_0$ and an exponent $\gamma$ are defined according to the equations:

$$\sum_{i=1}^{N} P_i = 1 \text{ where } P_i = \max(L_i^\gamma - L_0^\gamma, 0)$$

and $$\sum_{i=1}^{N} Q_i = 1 \text{ where } Q_i = \max(L_0^\gamma - L_i^\gamma, 0)$$

After each iterative step of the complete set of N members, one trial sequence is deleted from the less likely subset according to the probability Q and one sequence from the more likely subset is duplicated according to probability P. This process is equivalent to re-weighting the sequences of the original set by factors $L_i^\gamma$, so that the parameter $\lambda$ is thereby increased by $\gamma$ to $\lambda+\gamma$, without further ad hoc device.

The annealing terminates when $\lambda=1$, at which point the experimental data is being given full significance. The MCMC algorithm may then be terminated and the trial seqsequences under consideration, along with their probabilities, will represent the most probable sequences for the unknown peptide sample.

In order to calculate the likelihood factors required in the determination of the probabilities of each trial sequence, a fragmentation model is used which sums probabilistically over all the ways in which a trial sequence might fragment and give rise to peaks in the processable mass spectrum. This model should incorporate as much chemical knowledge concerning the fragmentation of peptides in the tandem mass spectrometer as is available at the time it is constructed. A preferred model incorporates the production of the following series of ions:

a) The b series, (ions representing the N-terminal amino acid residues and the loss of C-terminal amino acid residues);

b) The y" series, (ions representing the C-terminal amino acid residues and the loss of N-terminal amino acid residues);

c) The a series, (b ions which have lost CO); and d) z" series, (y" ions which have lost $NH_3$);

e) more general loss of $NH_3$ or $H_2O$.

The two main series of ions (y" and b) are represented in the preferred fragmentation model by Markov Chains, one for each series. In each chain, the probability that a particular ion is observed is dependent on the probability of its predecessor. For example, principally because of charge location, the observed y" ions in a fragmentation spectrum tend to form a coherent series starting with $y_1$ and usually continuing for some way with $y_2, y_3 \ldots$, perhaps fading out for a time but likely appearing again towards $y_{n-1}$ and finally the full molecule. A Markov chain models this behaviour by setting up the probability (P) of y ions being present as a recurrence relation:

$P(y_1) = p_1$ $P(y_r) = p_r P(y_{r-1}) + q_r (1 - P(y_{r-1}))$ for $r=2,3,4,\ldots, n$ where $P(y_r)$ is the probability of $y_r$ being present and the probability of $y_r$ being absent is $1-P(y_r)$. The coefficients p and q are transition probabilities that determine how likely the series is to begin, to end, and to (re-)start. Their values can be set according to the charge affinity of the residues allied to physical bond strengths. For example, a y series is likely to start and be present at and after a proline residue so that p would be assigned a higher value if the residue r were proline then if it were another residue.

A similar Markov Chain may be set up to represent the b ions, incorporating the observation that the $b_1$ ion is usually absent.

These Markov Chains are supplemented by introducing probabilities that the b series ions may also suffer loss of CO to form ions in the a series, and that y" series ions can lose $NH_3$ to form z" series ions and there may be more general loss of $NH_3$ or $H_2O$. The possibility that any fragment ion may lose either $NH_3$ or $H_2O$ is also incorporated into the model. Each possible process is assigned a probability which depends on the chemistry involved, for example, the probability of water loss increases with the number of hydroxyl groups on the fragment's side chains and would be zero if there are no such hydroxyl groups that could be lost.

The formation of Immonium ions (which are equivalent to the loss of CO and H from a single residue) is also incorporated in the fragmentation model. Only certain residues can generate these ions, and for those that do, appropriate probabilities are set. For example, histidine residues generally result in the formation of an immonium ion at mass 110.072 daltons, and the probability of this process is therefore set close to 100%. Finally, the fragmentation model allows for the formation of internal sequences starting at any residue, according to a probability appropriate for that particular residue. Internal sequences are often observed starting at proline residues, so that the probability of one starting at a proline residue is therefore set high.

It will be appreciated that the more realistic is the fragmentation model the faster and more faithful will be the inference of the sequence of the unknown peptide. Consequently, as the understanding of the chemical processes involved in the formation of the fragmentation spectra of peptides advances, it is within the scope of the invention to adjust the fragmentation model accordingly.

The fragmentation model is explicitly probabilistic, meaning that it produces a probability distribution over all the ways that a trial sequence might fragment (based on the fragmentation model) rather than a list of possible masses in a predicted spectrum. Thus, the likelihood factor is computed as the sum over all these many fragmentation possibilities, so that the fragmentation pattern for a trial sequence is automatically and individually adapted to the data comprised in the processable spectrum. In terms of probability theory, the likelihood factor of the processable spectrum D, given a particular trial sequence S is $$P(D \text{ GIVEN } S) = \sum_{f} P(D \text{ GIVEN } f) P(f \text{ GIVEN } S)$$

where $$\sum_{f}$$

represents the sum over all the permitted fragmentation patterns f, P(D GIVEN f) is the probability of the processable spectrum assuming the particular fragmentation pattern f, and P(f GIVEN S) is the probability of having fragmentation f from the trial sequence S. As explained, this sum can be integrated computationally in polynomial time rather than in a time proportional to the exponentially large number of fragmentation patterns themselves, which results in practical computational times of a minute or so for the whole MCMC process while providing a mathematically rigorous approach without limiting the trial sequences being considered.

As explained, the invention includes the use of such a probabilistic fragmentation model to calculate the probability that any given amino acid sequence could account for an experimentally observed peptide mass spectrum, irrespective of the origin of the sequence itself. In order to identify an unknown peptide or protein, therefore, trial sequences of appropriate molecular weight may be obtained from a database of known peptides and proteins. An experimental processable spectrum and molecular weight of the unknown peptide is first obtained as explained above. Trial sequences or, partial sequences are then pseudo-randomly selected from the database according to the criteria that they should have the molecular weight (within experimental error) of the unknown peptide. The fragmentation model (described above) is then used to calculate the probability that each trial sequence would account for the processable spectrum. The most probable trial sequences thus identified should then enable the unknown peptide to be identified, providing that its sequence is in fact comprised in the database. Because the fragmentation model is explicitly probabilistic, it requires no ad hoc scoring method to compare the processable spectrum with a spectrum predicted for a trial sequence, unlike the prior sequencing methods that are used in conjunction with existing databases. Not only is a meaningful probability figure calculated for a given trial sequence, but the probability of the assignment of each peak in the processable spectrum to a given amino acid residue loss is also inherently calculated. This leads greater confidence in the identification of the peptide and indicates the regions in a sequence about which some doubt may exist if a single match of very high probability cannot be achieved.

EXAMPLE

Figure 3:
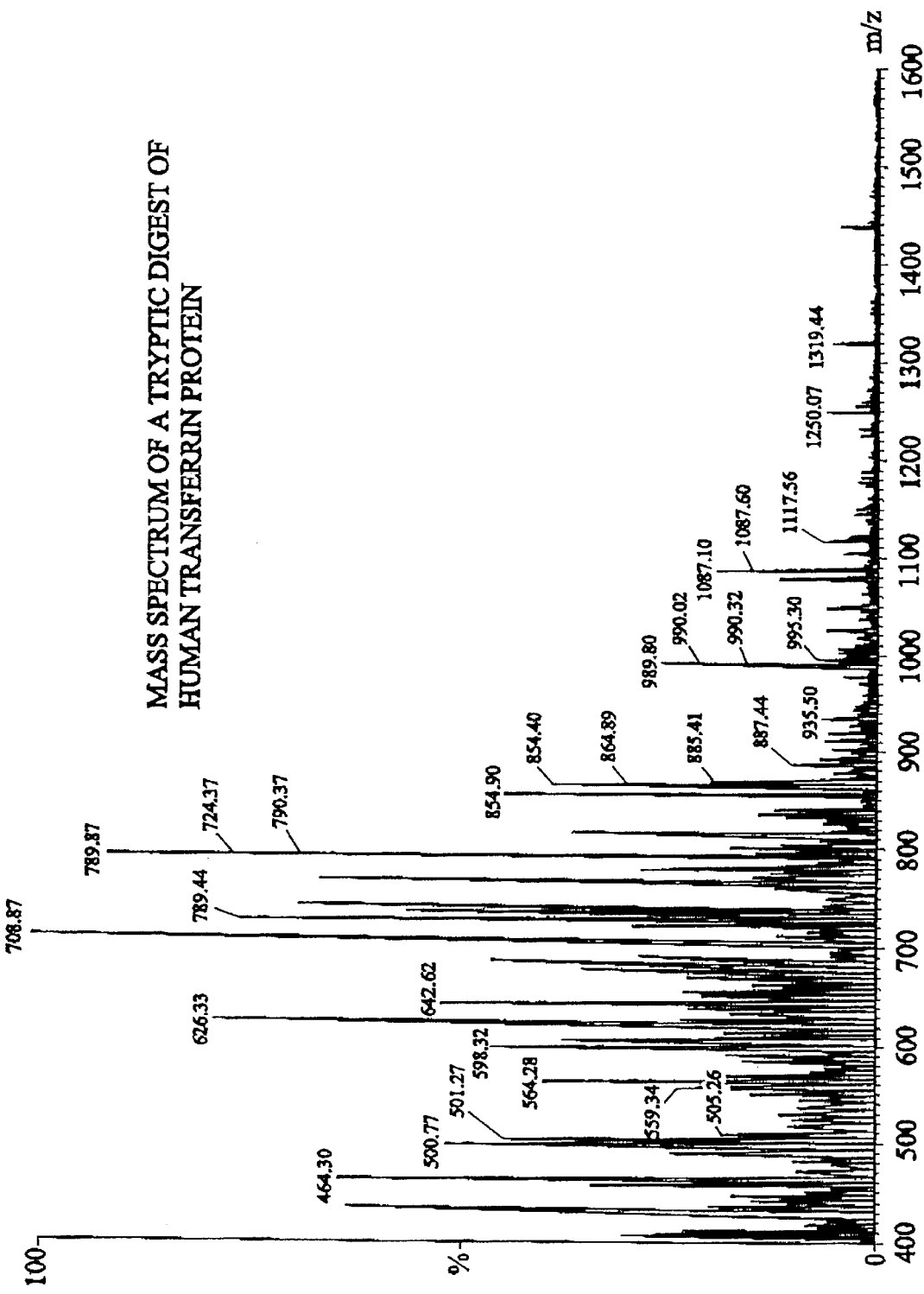
FIG. 3 is a mass spectrum of a tryptic digest of Human Transferrin Precursor Protein.
Figure 4:
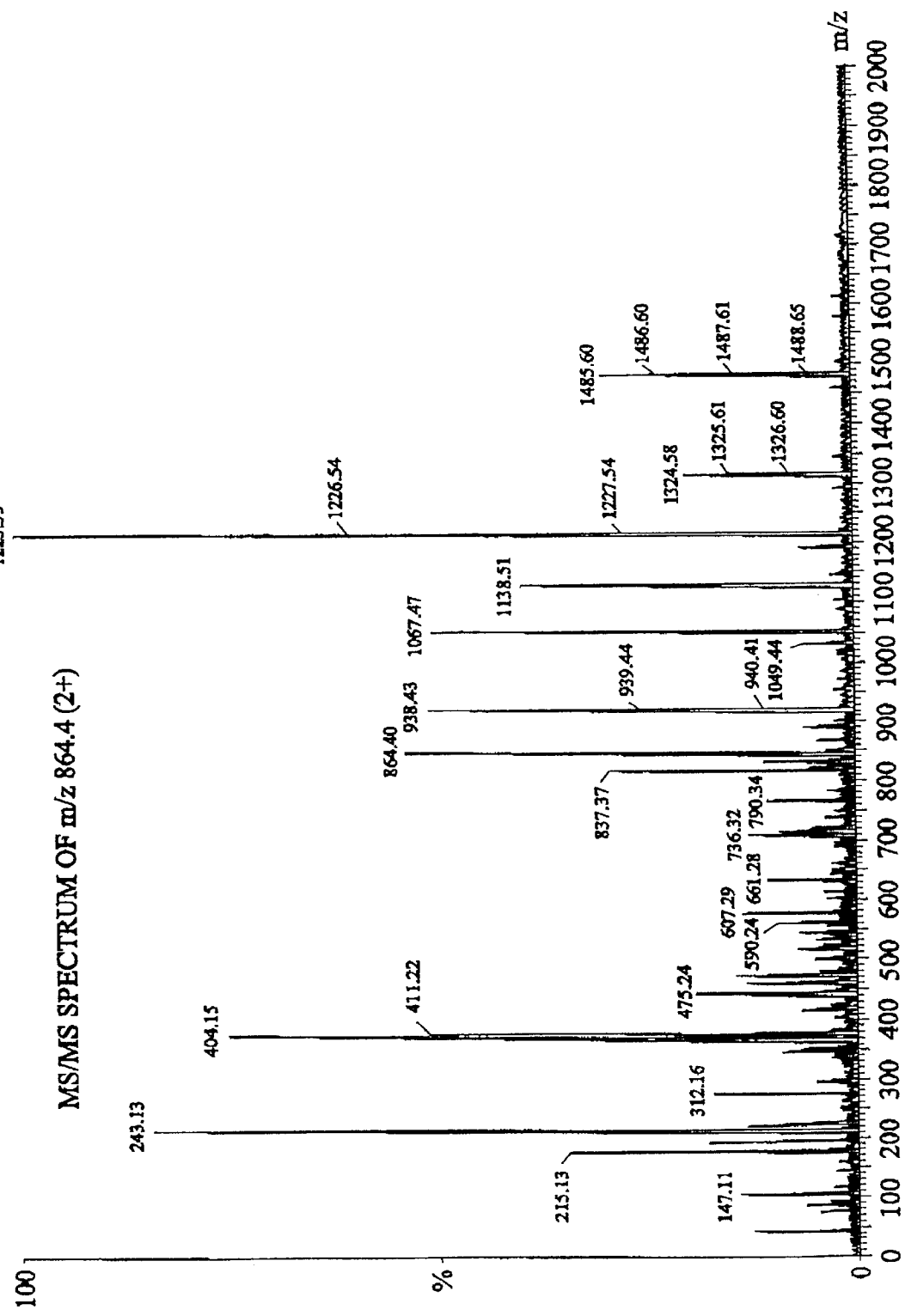
FIG. 4 is a fragmentation mass spectrum of the m/z=864.4 peak in the spectrum of FIG. 3.
Figure 5:
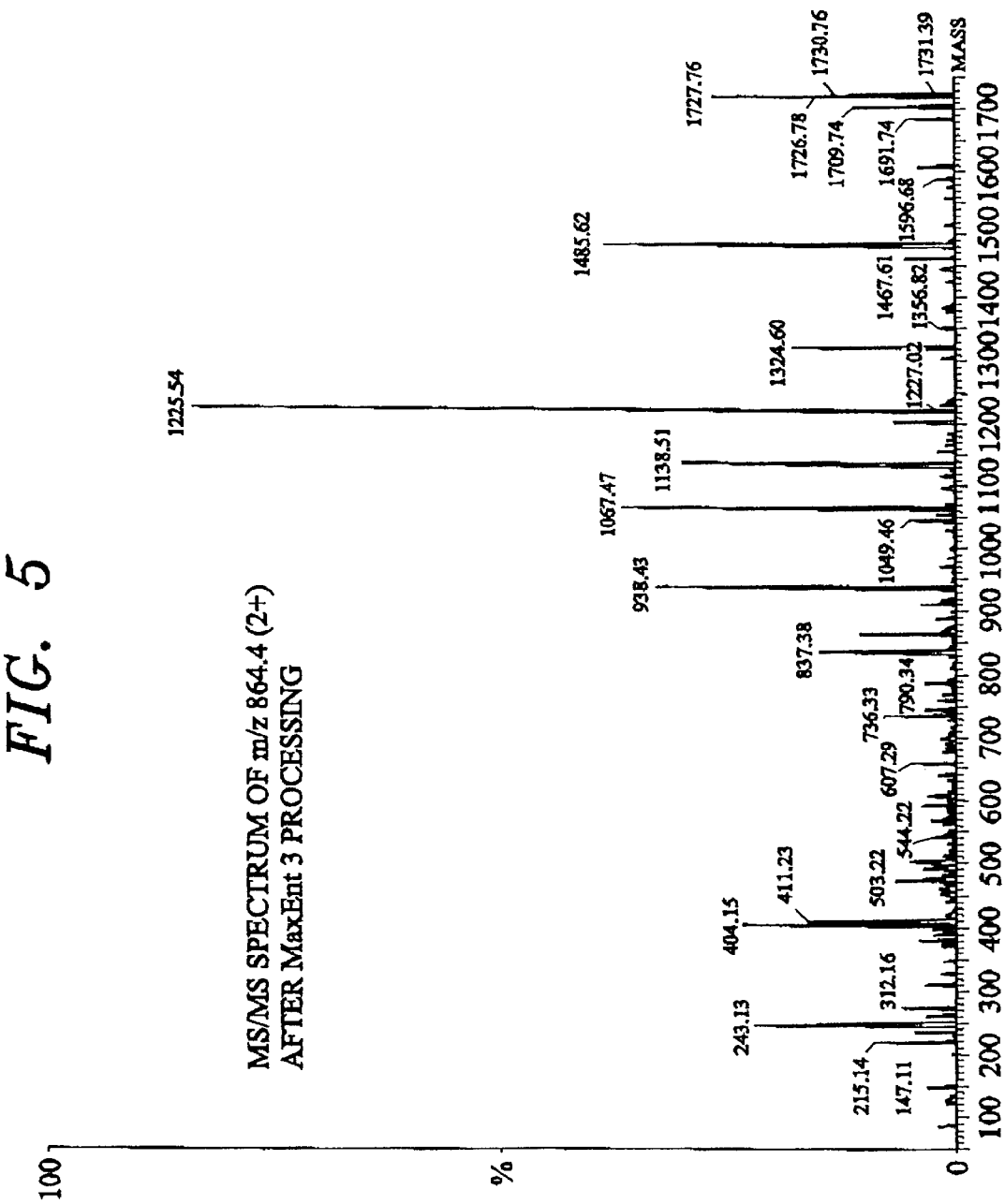
FIG. 5 is the spectrum of FIG. 4 after processing with the program "MaxEnt3™"

A sample of human transferrin precursor in which the cysteine groups were protected by carboxymethylation was digested using trypsin to generate a mixture of peptides which was analyzed by a method according to the invention. FIG. 3 shows the electrospray mass spectrum of the digest produced by using the first stage quadrupole mass analyzer 7 in the spectrometer of FIG. 1 in a non mass-selective mode. The analyzer 7 was then tuned to transmit ions of mass-to-charge ratio 864.4 (actually a doubly charged ion) into the collision cell 9 (FIG. 1) and the resultant fragmentation spectrum is shown in FIG. 4. A processable mass spectrum (FIG. 5) was then produced in accordance with the invention using the program "MaxEnt3™", as discussed above. The data on which the spectrum of FIG. 5 was based was then processed by the preferred method of the invention and the most probable sequences shown in Table 2 were predicted. Thus, the sequence LECVSAETTEDCLAK is by far the most likely sequence. Because the method of the invention is fully probabilistic, the probability of the assignment of each amino acid comprised in the proposed sequences is automatically predicted, as shown in Table 3 for the most probable sequence. In Table 3, the rows labeled a, b, y, and z are the predicted mass-to-charge ratios for the a, b, y" and z" series for the sequence, and underlined entries indicate the ions which are well detected in the processable spectrum.

TABLE 2

Most probable sequences for m/c 864.4

| No | Sequence | % probability |
|---|---|---|
| 1 | LECVSAETTEDCLAK | 97.76 |
| 2 | ELCVSAETTEDCLAK | 1.71 |
| 3 | LECVSAETTELEDCK | 0.35 |
| 4 | LECVSAETTEDLCAK | 0.07 |
| 5 | LECVSAETTEELDCK | 0.05 |
| 6 | LECVSAETTEDLCEK | 0.01 |
| 7 | LECVSAETTEDVDMK | <0.01 |
| | Etc. | |

It can be seen that most of the predicted ions comprised in the y" and b series have been detected in the processable spectrum, so that the probabilities assigned to the amino acid residues comprised in the most probable sequence are very high. The second most probable sequence, which differs from the most probable sequence merely by the inversion of the first two residues, is assigned a probability of only 1.7%, to be compared with the probability of 97.6% for the most probable sequence. In fact, the $864.4^{++}$ ion represents the known T42 fragment in the digest of the protein (see Table 4) and the most probable sequence is the correct one. (In Table 4, the symbol B is used to represent the carboxymethylated cysteine residues which are listed as C in the above. Also, the residues leucine (L) and isoleucine (I) have identical molecular weights and so cannot be distinguished by mass spectrometry. Both are represented by L in Table 2, but are distinguished in Table 4.) The position of the T42 fragment in the complete protein sequence is shown underlined in Table 5.

Figure 6:
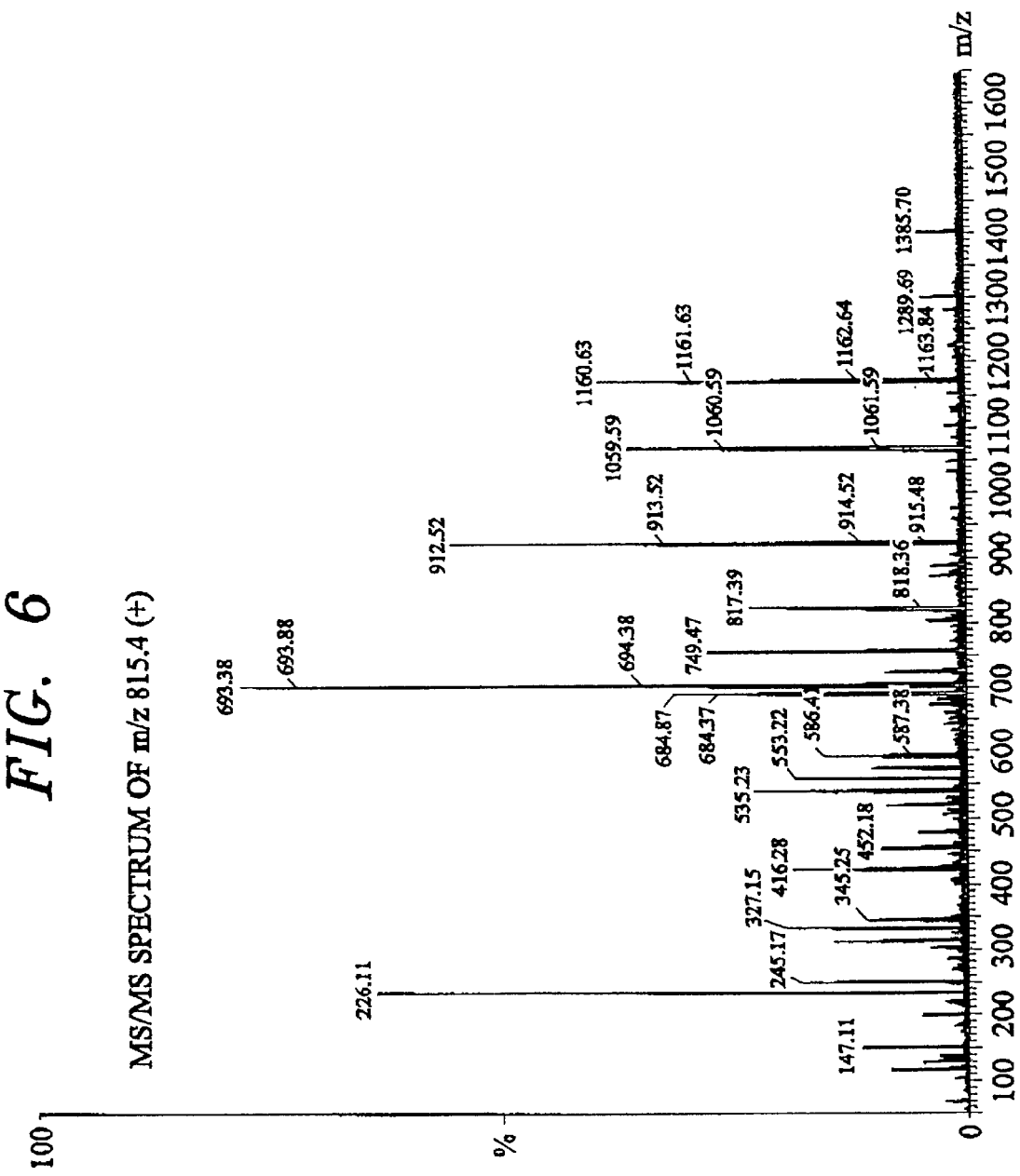
FIG. 6 is a fragmentation spectrum of the m/z=815.4 peak in the spectrum of FIG. 3.
Figure 7:
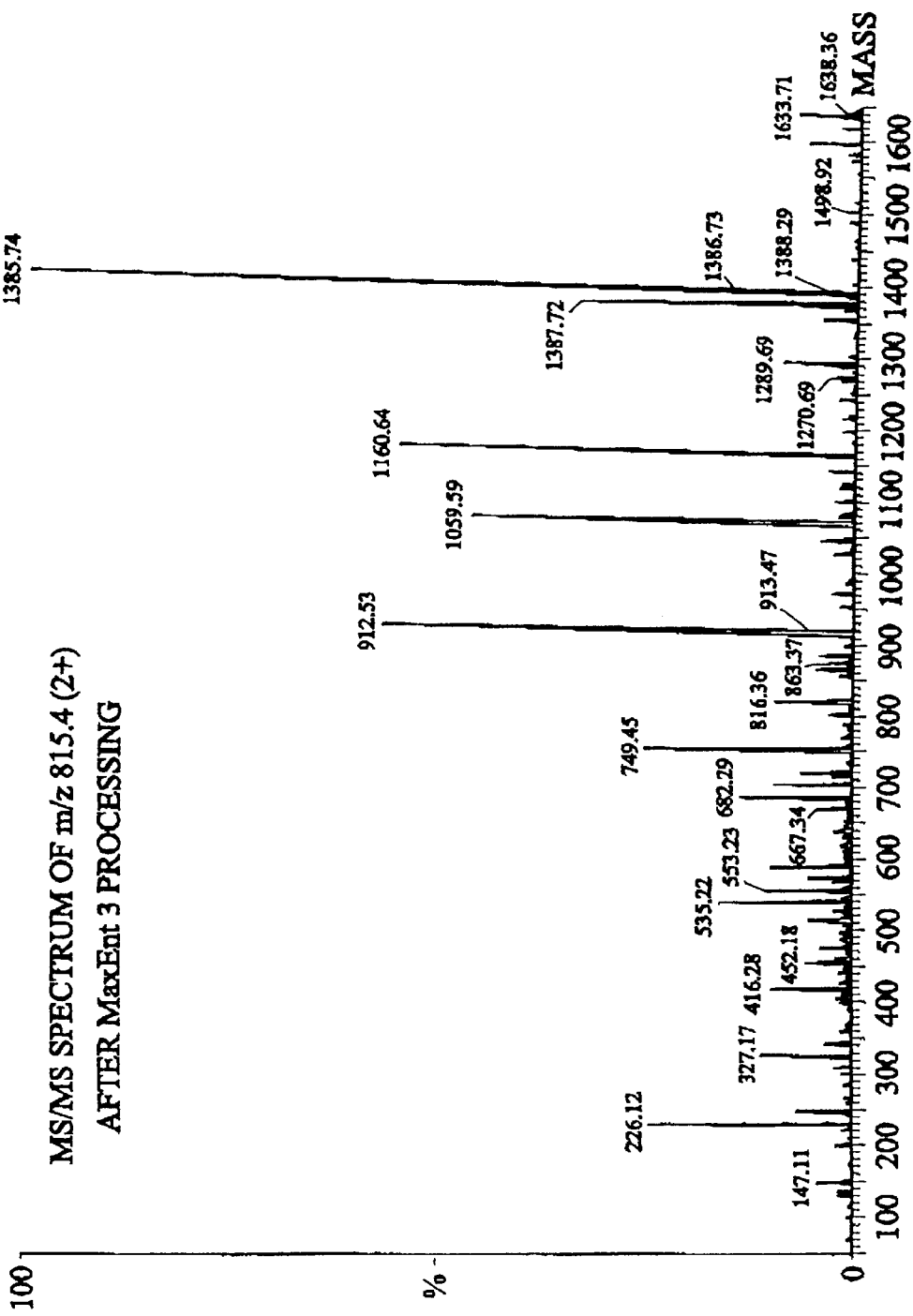
FIG. 7 is the spectrum of FIG. 6 after processing with the program "MaxEnt3™".

The fragmentation spectrum of a second peak (815.4) in the mass spectrum of FIG. 3 was also determined and is shown in FIG. 6. A processable mass spectrum (FIG. 7) was then produced from the data comprising the FIG. 6 mass spectrum using the program "MaxEnt 3™". The data so produced was then processed according to the method of invention and the most probable sequences shown in Table 6 were predicted. In this case, there are two sequences predicted with similar probabilities, and many others with very small probabilities. The fragment is in fact the known T11 fragment of the protein digest (see Table 4), and the actual sequence has in fact been correctly predicted as the most probable sequence in Table 6 by a significant margin.

TABLE 6

Most Probable Sequences for m/z 815.4

| No | Sequence | % Probability |
|---|---|---|
| 1 | EDPQTFYYAVAVVK | 57.95 |
| 2 | DEPQTFYYAVAVVK | 42.03 |
| 3 | EDPQTFYYAVVAVK | <0.001 |
| 4 | EDPQTFYYAAVVVK | <0.001 |
| 5 | DEPQTFYYALVVK | <0.001 |
| 6 | EDPQTFYYALVVK | <0.001 |
| | Etc. | |

The position of the T11 fragment is shown by double underlining in the complete sequence listed in Table 5. The second most probable sequence in Table 6 differs only from the most probable one by the inversion of the first two residues, and it can be seen from the individual probability assignments to the various predicted residues (Table 7) that there is much less certainty about the assignment of the first two residues than there is about the assignment of the others.

This example clearly shows the advantage of a rigorous application of probability calculus in comparison with the ad hoc methods of predicting sequences from mass spectral data described in the prior art. From the figures in table 7 it is possible to be certain about the sequence of the central part of the peptide for which very high probabilities are reported, and any doubt that may linger about the complete sequence can be shown to be limited to the first two residues. Further, the degree of certainty of the assignment of each residue can be quantified from the figures in Tables 3 and 7, greatly improving the confidence that can be placed in sequences predicted by methods according to the invention.

TABLE 3

Most Probable Sequence, m/z 864.4

| Residue | L | E | C | V | S | A | E | T | T | E | D | C | L | A | K |
|---|---|---|---|---|---|---|---|---|---|---|---|---|---|---|---|
| Prob. (%) | 98.3 | 98.3 | 99.9 | 100 | 100 | 100 | 100 | 100 | 100 | 99.99 | 99.6 | 99.5 | 99.5 | 99.6 | 100 |
| a | 86.10 | 215.14 | 376.15 | 475.22 | 562.25 | 633.29 | 762.33 | 863.38 | 964.43 | 1093.47 | 1208.50 | 1369.51 | 1482.60 | 1553.64 | 1681.73 |
| b | 114.09 | 243.13 | 404.15 | 503.22 | 590.25 | 661.29 | 790.33 | 891.38 | 992.42 | 1121.47 | 1236.49 | 1397.51 | 1510.59 | 1581.63 | 1709.72 |
| y" | 1727.74 | 1614.65 | 1485.61 | 1324.59 | 1225.53 | 1138.49 | 1067.46 | 938.41 | 837.37 | 736.32 | 607.28 | 492.25 | 331.23 | 218.15 | 147.11 |
| z" | 1710.71 | 1597.62 | 1468.58 | 1307.56 | 1208.50 | 1121.46 | 1050.43 | 921.38 | 820.34 | 719.29 | 590.25 | 475.22 | 314.20 | 201.22 | 130.08 |

TABLE 4

HUMAN TRANSFERRIN PRECURSOR PROTEIN

| Frag # | Res. | Sequence | Theor. | (M + H) | (M + 2H) |
|---|---|---|---|---|---|
| T61 | 565–571 | (K)NPDPWAK(N) | 826.40 | 827.41 | 414.21 |
| T33 | 316–323 | (K)DSAHGFUC(V) | 873.43 | 874.44 | 437.73 |
| T25 | 252–258 | (R)KPVDEYK(D) | 877.45 | 878.46 | 439.74 |
| T50 | 468–475 | (K)SBHTAVGR(T) | 887.39 | 888.40 | 444.70 |
| T16 | 136–143 | (K)SBHTGLGR(S) | 887.39 | 888.40 | 444.70 |
| T73 | 652–659 | (R)DDTVBLAK(L) | 921.41 | 922.42 | 461.71 |
| T65 | 601–609 | (R)APNHAWTR(K) | 963.53 | 964.53 | 482.77 |
| T21 | 216–225 | (K)DGAGDVAFVK(H) | 977.48 | 978.49 | 489.75 |
| T9 | 62–69 | (K)ASYLDBIR(A) | 997.45 | 998.46 | 499.73 |
| T76 | 669–676 | (K)YLGEEYVK(A) | 999.49 | 1000.50 | 500.75 |
| T60 | 554–564 | (K)HQTVPQNTGGK(N) | 1165.58 | 1166.59 | 583.80 |
| T13 | 123–132 | (K)DSGFQNNQLR(G) | 1194.55 | 1195.55 | 598.28 |
| T39 | 363–371 | (K)WBALSHHER(L) | 1195.52 | 1196.53 | 598.77 |
| T47 | 454–464 | (K)SASDLTWDNUC(G) | 1248.60 | 1249.61 | 625.31 |
| T22 | 226–236 | (K)HSTIFENLANK(A) | 1272.65 | 1273.65 | 637.33 |
| T31 | 300–310 | (K)EFQLFSSPHGK(D) | 1275.62 | 1276.63 | 638.82 |
| T41 | 374–384 | (K)BDEWSVNSVGK(I) | 1280.53 | 1281.54 | 641.28 |
| T57 | 531–541 | (K)EGYYGYTGAFR(B) | 1282.56 | 1283.57 | 642.29 |
| T4 | 2737 | (R)WBAVSEHEATK(B) | 1317.57 | 1318.57 | 659.79 |
| T63 | 577–587 | (K)DYELLBLGTR(K) | 1354.61 | 1355.62 | 678.31 |
| T7 | 47–60 | (K)BVIPSDGPSVABVK(K) | 1415.70 | 1416.70 | 708.86 |
| T44 | 421433 | (K)BGLVPVLAENYNK(S) | 1476.73 | 1477.74 | 739.37 |
| T36 | 332–343 | (K)MYLGYEYVTAIR(N) | 1477.73 | 1478.74 | 739.87 |
| T79 | 684–696 | (K)BSTSSLLEABTFR(R) | 1532.65 | 1533.66 | 767.33 |
| T24 | 240–251 | (R)DQYELLBLDNTR(K) | 1539.69 | 1540.70 | 770.85 |
| TS1 | 476–489 | (R)TAGWNIPMGLLYNK(I) | 1576.81 | 1577.82 | 789.41 |
| T53 | 495–508 | (R)FDEFFSEGBAPGSK(K) | 1577.63 | 1578.64 | 789.83 |
| T64 | 588–600 | (R)KPVEEYANBHLAR(A) | 1586.75 | 1587.76 | 794.38 |
| T11 | 108–121 | (K)EDPQTFYYAVAVVK(K) | 1628.81 | 1629.82 | 815.41 |
| T26 | 259–273 | (K)DBHLAQVPSHTVAR(S) | 1689.83 | 1690.83 | 845.92 |
| T56 | 516–530 | (K)LBMGSGLNLBEPNNK(E) | 1707.73 | 1708.73 | 854.87 |
| T42 | 385–399 | (K)IEBVSAETTEDBIAK(I) | 1726.73 | 1727.74 | 864.37 |
| T38 | 347–362 | (R)EGTBPEAPTDEBKPVK(W) | 1818.77 | 1819.77 | 910.39 |
| T28 | 279–295 | (K)EDLIWELLNQAQEHFGK(D) | 2069.02 | 2070.03 | 1035.52 |
| T45 | 434–452 | (K)SDNBEDTPEAGYFAVAV | 2071.90 | 2072.91 | 1036.96 |

TABLE 5

```
            HUMAN TRANSFERRIN PRECURSOR PROTEIN
      Average Mass = 79371.6670, Monoisotopic Mass = 79319.8350
                 N-Terminus = H, C-Terminus = OH
         Modified amino acids: Cmc(B) = Carboxymethylcysteine 1  MRLAV GALLV BAVLG LBLAV PDKTV RWBAV SEHEA TKBQS FRDHM KSVIP SDGPS VABVK KASYL DBIRA
      IAANE ADAVT LDAGL VYDAY LAPNN LKPVV AEFYG SKEDP
 111  QTFYY AVAVV KKDSG FQMNQ LRGKK SBHTG LGRSA GWNIP IGLLY BDLPE PRKPL EKAVA NFFSG SBAPB
      ADGTD FPQLB QLBPG BGBST LNQYF GYSGA FKBLK DGAGD
```

TABLE 5-continued

HUMAN TRANSFERRIN PRECURSOR PROTEIN
Average Mass = 79371.6670, Monoisotopic Mass = 79319.8350
N-Terminus = H, C-Terminus = OH
Modified amino acids: Cmc(B) = Carboxymethylcysteine

```
221 VAFVK HSTIF ENLAN KADRI QYELL BLDNT RKPVD EYKDB HLAQV PSHTV VARSM GGKED LIWEL LNQAQ
    EHFGK DKSKE FQLFS SPHGK DLLFK DSAHG FLKVP PRMDA
331 KMYLG YEYVT AIRNL REGTB PEAPT DEBKP VKWBA LSHHE RLKBD EWSVN SVGKI EBVSA ETTED BIAKI
    MNGEA DAMSL DGGFV YIAGK BGLVP VLAEN YNKSD NBEDT
441 PEAGY FAVAV VKKSA SDLTW DNLKG KKSBH TAVGR TAGWN IPMGL LYNKI NHBRF DEFFS EGBAP GSKKD
    SSLBK LBMGS GLNLB EPNNK EGYYG YTGAF RBLVE KGDVA
551 FVKHQ TVPQN TGGKN PDPWA KNLNE KDYEL LBLDG TRKPV EEYAN BHLAR APNHA VVTRK DKEAB VHKIL
    RQQQH LFGSN VTDBS GNFBL FRSET KDLLF RDDTV BLAKL
661 HDRNT YEKYL GEEYV KAVGN LRKBS TSSLL EABTF RRP
```

Single Underline = T42 fragment
Double Underline = T11 fragment

TABLE 7

Most Probable Sequence, m/z 815.4

| Residue | E | D | P | Q | T | F | Y | Y | A | V | A | V | V | K |
|---|---|---|---|---|---|---|---|---|---|---|---|---|---|---|
| Prob. % | 57.96 | 57.96 | 100.0 | 100.0 | 100.0 | 100.0 | 100.0 | 100.0 | 100.0 | 100.0 | 99.99 | 99.99 | 100.0 | 100.0 |
| a | 102.06 | 217.08 | 314.14 | 442.19 | 543.24 | 690.31 | 853.37 | 1016.44 | 1087.47 | 1186.54 | 1257.58 | 1356.65 | 1455.72 | 1583.81 |
| b | 130.05 | 245.08 | 342.13 | 470.19 | 571.24 | 718.30 | 881.37 | 1044.43 | 1115.47 | 1214.54 | 1285.57 | 1384.64 | 1483.71 | 1611.81 |
| y" | 1629.82 | 1500.77 | 1385.75 | 1288.69 | 1160.64 | 1059.59 | 912.52 | 749.46 | 586.39 | 515.36 | 416.29 | 345.25 | 246.18 | 147.11 |
| z" | 1612.79 | 1483.74 | 1368.72 | 1271.66 | 1143.61 | 1042.56 | 895.49 | 732.43 | 569.36 | 498.33 | 399.26 | 328.22 | 229.15 | 130.08 |

What is claimed is:

1. A method of identifying the most likely amino acid sequence which would account for a mass spectrum obtained from a peptide having an unknown sequence of amino acids, said method comprising the steps of:
   producing a processable mass spectrum from the peptide;
   choosing a limited number of trial sequences of amino acids which are consistent with a prior probability distribution; and
   iteratively modifying said trial sequences through a terminated Markov Chain Monte Carlo algorithm to generate new trial sequences of amino acids consistent with said prior probability distribution, using at each stage modifications which lie within said prior probability distribution, calculating the probability of each of said trial sequences accounting for said processable mass spectrum, and accepting or rejecting each of said trial sequences according to said calculated probability and the mathematical principle of detailed balance.

2. A method as claimed in claim 1, wherein the probability of a particular trial sequence accounting for said processable mass spectrum is calculated using Bayes' theorem wherein said prior probability distribution is multiplied by a likelihood factor which reflects the degree of agreement between a spectrum predicted for a said trial sequence and the processable mass spectrum.

3. A method as claimed in claim 2, wherein said likelihood factor is determined using a fragmentation model which sums probabilistically over all the ways in which a trial sequence might fragment and give rise to peaks in said processable mass spectrum.

4. A method as claimed in claim 3, wherein said fragmentation model sums over all the ways in which a trial sequence might fragment in a time proportional to the number of amino acid residues in the peptide.

5. A method as claimed in claim 3, wherein said fragmentation model models the fragmentation of a trial sequence by means of Markov chains.

6. A method as claimed in claim 3, wherein said fragmentation model includes the production of at least the b and y" series of ions, wherein said b series is defined as comprising ions representing the N-terminal residue of the trial sequence and the loss of C-terminal amino acid residues and said y" series is defined as comprising ions representing the C-terminal residue and the loss of N-terminal amino acid residues.

7. A method as claimed in claim 6, wherein said fragmentation model includes the production of the a series of ions, wherein said a series is defined as comprising b series ions which have lost CO.

8. A method as claimed in claim 6, wherein said fragmentation model includes the production of the z" series of ions, wherein said z" series is defined as comprising y" series ions which have lost $NH_3$.

9. A method as claimed in claim 6, wherein said fragmentation model includes the production of ions which have lost $NH_3$ and/or $H_2O$.

10. A method as claimed in claim 6, wherein said fragmentation model includes the production of immonium ions equivalent to the loss of CO and H from amino acid residues.

11. A method as claimed in claim 6, wherein said fragmentation model includes the generation of sub-sequences of amino acids which begin and end at amino acid residues internal to the unknown peptide.

12. A method as claimed in claim 2, wherein said likelihood factor is controlled by a simulated annealing algorithm wherein said likelihood factor is raised to a fractional power which is initially zero and which is gradually increased.

13. A method as claimed in claim 12, wherein the generation and testing of new trial sequences is continued until said simulated annealing algorithm raises the likelihood factor to the power of one.

14. A method as claimed in claim 1, wherein the number of trial sequences is limited to approximately 100.

15. A method as claimed in claim 1, wherein said trial sequences are chosen pseudo-randomly from said prior probability distribution.

16. A method as claimed in claim 1, wherein said prior probability distribution is determined from the natural abundance of each of the amino acid residues comprised in the trial sequence.

17. A method as claimed in claim 1, wherein said prior probability distribution comprises sequences of amino acids based on the twenty most common amino acid residues.

18. A method as claimed in claim 1, wherein said prior probability distribution comprises sequences of amino acids having a molecular weight within a predetermined range of the approximate molecular weight of the sample.

19. A method as claimed in claim 18, wherein said predetermined range is ±5 Daltons.

20. A method as claimed in claim 18, wherein said predetermined range is ±0.5 Daltons.

21. A method as claimed in claim 1, wherein said Markov Chain Monte Carlo algorithm generates new trial sequences by reversing a contiguous sub-sequence with randomly chosen end points.

22. A method as claimed in claim 1, wherein said Markov Chain Monte Carlo algorithm generates new trial sequences by cycling a contiguous sub-sequence with randomly chosen end points.

23. A method as claimed in claim 1, wherein said Markov Chain Monte Carlo algorithm generates new trial sequences by permuting a contiguous sub-sequence with randomly chosen end points.

24. A method as claimed in claim 1, wherein said Markov Chain Monte Carlo algorithm generates new trial sequences by replacing a contiguous sub-sequence with randomly chosen end points with another sub-sequence of approximately the same nominal mass.

25. A method as claimed in claim 1, wherein said Markov Chain Monte Carlo algorithm generates new trial sequences by exchanging the C-terminus and N-terminus ends of two sequences to preserve nominal mass.

26. A method as claimed in claim 1, wherein said processable mass spectrum comprises the observed mass spectrum.

27. A method as claimed in claim 1, wherein said processable mass spectrum is obtained by converting multiply-charged ions and isotopic clusters of ions to a single intensity value at the mass-to-charge ratio corresponding to a singly-charged ion of the lowest mass isotope.

28. A method as claimed in claim 27, further comprising the step of calculating an uncertainty value for the actual mass and the probability that a peak at that is mass-to-charge ratio has actually been observed.

29. A method as claimed in claim 28, wherein the uncertainty value of a peak may be based on the standard deviation of a Gaussian peak representing the processed peak and the probability that a peak is actually observed may be based on the signal-to-noise ratio of the peak in the observed spectrum.

30. A method of calculating the probability that an experimentally determined mass spectrum of a peptide or similar molecule may be accounted for by a given sequence of amino acids, comprising the step of:

using a fragmentation model which sums probabilistically over all the ways that said given sequence might fragment, said fragmentation model modelling the fragmentation of a trial sequence by means of Markov chains.

31. A method as claimed in claim 30, wherein the experimentally determined mass spectrum is a processable spectrum.

32. A method as claimed in claim 31, wherein said processable mass spectrum is obtained by converting multiply-charged ions and isotopic clusters of ions to a single intensity value at the mass-to-charge ratio corresponding to a singly-charged ion of the lowest mass isotope.

33. Apparatus for identifying the most likely sequences of amino acids in an unknown peptide, said apparatus comprising a mass spectrometer for generating a mass spectrum of said unknown peptide and data processing means programmed to:

(a) process data generated by said mass spectrometer to produce a processable mass spectrum;

(b) choose a limited number of trial amino acid sequences that are consistent with a prior probability distribution; and (c) iteratively modify said trial sequences through a terminated Markov Chain Monte Carlo algorithm to generate new trial sequences consistent with said prior probability distribution, using at each stage modifications which lie within said prior probability distribution, calculate the probability of each of said trial sequences accounting for said processable mass spectrum, and accept or reject each of said trial sequences according to said calculated probability and the mathematical principle of detailed balance.

34. Apparatus as claimed in claim 33, wherein said mass spectrometer comprises a tandem mass spectrometer.

35. Apparatus as claimed in claim 33, wherein said mass spectrometer comprises a time of flight mass analyzer.

36. Apparatus as claimed in claim 33, further comprising an electrospray ionization source into which an unknown peptide sample may be introduced.

* * * * *